(12) United States Patent
Tucker

(10) Patent No.: US 10,816,653 B2
(45) Date of Patent: Oct. 27, 2020

(54) SWIMMING SPEEDOMETER SYSTEM WITH NEAR-EYE DISPLAY

(71) Applicant: Robert Stephen Tucker, New York, NY (US)

(72) Inventor: Robert Stephen Tucker, New York, NY (US)

(73) Assignee: Swimmetric, LLC, New York, NY (US)

( * ) Notice: Subject to any disclaimer, the term of this patent is extended or adjusted under 35 U.S.C. 154(b) by 715 days.

(21) Appl. No.: 15/360,745

(22) Filed: Nov. 23, 2016

(65) Prior Publication Data

US 2017/0146644 A1 May 25, 2017

Related U.S. Application Data

(60) Provisional application No. 62/259,813, filed on Nov. 25, 2015, provisional application No. 62/330,759, filed on May 2, 2016.

(51) Int. Cl.
*G01S 11/14* (2006.01)
*A63B 33/00* (2006.01)
(Continued)

(52) U.S. Cl.
CPC ............ *G01S 11/14* (2013.01); *A63B 33/002* (2013.01); *A63B 71/0622* (2013.01); *G01P 1/08* (2013.01);
(Continued)

(58) Field of Classification Search
CPC ............ A63B 2208/03; A63B 2220/13; A63B 2220/30; A63B 2225/54; A63B 2244/20;
(Continued)

(56) References Cited

U.S. PATENT DOCUMENTS 4,776,045 A * 10/1988 Mysliwiec ........... A63B 33/002
2/426
4,961,626 A 10/1990 Fournier, Jr. et al.
(Continued)

FOREIGN PATENT DOCUMENTS

GB 2424820 A 10/2006

OTHER PUBLICATIONS

Medwin, Speed of sound in water a simple equation for realistic parameters, Journal of the Acoustical Society of America, 1975 (Year: 1975).*
(Continued)

*Primary Examiner* — Kyle R Quigley
(74) *Attorney, Agent, or Firm* — Davis, Malm & D'Agostine, P.C.; Richard L. Sampson

(57) ABSTRACT

An apparatus and method for measuring a swimmer's speed and conveying the speed to the swimmer in real time includes a plurality of ultrasonic beacons each having a transducer configured to emit ultrasonic signals in a pool or other body of water within which the swimmer is swimming. A wearable, waterproof, ultrasonic receiver worn by the swimmer, receives the ultrasonic signals and generates corresponding signal data. The receiver's microcontroller captures and uses the signal data to calculate the swimmer's position and speed in real time, and conveys this information to a wearable, waterproof, user interface device worn by the swimmer, the user interface device including a near-eye display disposed on the swimmer's googles.

26 Claims, 9 Drawing Sheets

(51) Int. Cl.
   *A63B 71/06* (2006.01)
   *G06F 1/16* (2006.01)
   *G01P 1/08* (2006.01)
   *G02B 27/01* (2006.01)
   *G16H 20/30* (2018.01)
   *B63C 11/12* (2006.01)
   *A63B 24/00* (2006.01)

(52) U.S. Cl.
   CPC ......... *G02B 27/01* (2013.01); *G02B 27/0101* (2013.01); *G02B 27/017* (2013.01); *G02B 27/0172* (2013.01); *G02B 27/0176* (2013.01); *G02B 27/0179* (2013.01); *G06F 1/163* (2013.01); *G06F 1/1654* (2013.01); *G16H 20/30* (2018.01); *A63B 24/0062* (2013.01); *A63B 2024/0071* (2013.01); *A63B 2033/004* (2013.01); *A63B 2071/0655* (2013.01); *A63B 2071/0666* (2013.01); *A63B 2208/03* (2013.01); *A63B 2209/10* (2013.01); *A63B 2210/50* (2013.01); *A63B 2220/10* (2013.01); *A63B 2220/13* (2013.01); *A63B 2220/17* (2013.01); *A63B 2220/30* (2013.01); *A63B 2220/40* (2013.01); *A63B 2220/80* (2013.01); *A63B 2220/803* (2013.01); *A63B 2220/833* (2013.01); *A63B 2220/836* (2013.01); *A63B 2225/50* (2013.01); *A63B 2225/54* (2013.01); *A63B 2244/20* (2013.01); *B63C 2011/121* (2013.01); *G02B 2027/014* (2013.01); *G02B 2027/0143* (2013.01); *G02B 2027/0178* (2013.01)

(58) Field of Classification Search
   CPC ... A63B 33/002; A63B 71/0622; G01S 11/14; G01S 11/16; G01S 5/30; G06F 1/163
   See application file for complete search history.

(56) References Cited

U.S. PATENT DOCUMENTS

| | | |
|---|---|---|
| 5,446,506 A | 8/1995 | Dawklins, Jr. |
| 5,585,871 A | 12/1996 | Linden |
| 5,685,722 A | 11/1997 | Taba |
| 5,767,417 A | 6/1998 | Parris et al. |
| 5,815,538 A * | 9/1998 | Grell .......................... G01S 5/10 342/413 |
| D470,880 S | 2/2003 | Sakai |
| 6,868,360 B1 | 3/2005 | Olstad et al. |
| 6,870,466 B2 | 3/2005 | Rust et al. |
| 7,185,983 B2 | 3/2007 | Nelson et al. |
| 7,345,958 B1 | 3/2008 | Kneafsey |
| 8,317,659 B2 | 11/2012 | Woodson |
| 8,406,085 B2 | 3/2013 | Sakita |
| 8,472,285 B2 | 6/2013 | Day |
| 9,266,006 B2 | 2/2016 | Herold |
| 2003/0117369 A1* | 6/2003 | Spitzer ................... A61B 3/113 345/156 |
| 2009/0141591 A1 | 6/2009 | Basilico |
| 2009/0219785 A1* | 9/2009 | Van "T Klooster ...... G01S 5/30 367/124 |
| 2009/0301185 A1 | 10/2009 | Duk |
| 2010/0030482 A1 | 2/2010 | Li |
| 2011/0149694 A1 | 6/2011 | Sakita |
| 2012/0226438 A1 | 9/2012 | Souza |
| 2013/0222213 A1 | 8/2013 | Abdollahi et al. |
| 2013/0241468 A1* | 9/2013 | Moshfeghi ............... H02J 7/025 320/107 |
| 2014/0009838 A1 | 1/2014 | Weber et al. |
| 2014/0200116 A1 | 7/2014 | Boutov et al. |
| 2015/0382085 A1* | 12/2015 | Lawrie-Fussey ........................... G06K 19/0717 340/870.07 |
| 2016/0154241 A1 | 6/2016 | Alhashim |

OTHER PUBLICATIONS

Hereman et al., Determination of a Position in Three Dimensions Using Trilateration and Approximate Distances, Decision Sciences, 1995 (Year: 1995).*
International Search Report and Written Opinion for PCT/US2017/062979 dated Feb. 6, 2018 by ISA/US; references cited herein.
Supplementary Partial EP Search Report for EP17873414 dated Aug. 23, 2019; pp. 1-6; Munich, DE.
Provisional Opinion Accompanying the Partial Search Report for EP17873414 dated Aug. 23, 2019; pp. 1-9; Munich, DE.
Supplementary Partial EP Search Report for EP17873414 dated Nov. 26, 2019; pp. 1-16; Munich, DE.

* cited by examiner

SWIMMING SPEEDOMETER SYSTEM WITH NEAR-EYE DISPLAY

RELATED APPLICATION

This application claims the benefit of U.S. Provisional Patent Application Ser. No. 62/259,813 entitled Instantaneous Swimming Speedometer System, filed on Nov. 25, 2015, and claims the benefit of U.S. Provisional Patent Application Ser. No. 62/330,759 entitled Low-power, Near-Eye Display Module for Conveying Information by Text, filed on May 2, 2016, the contents both of which are incorporated herein by reference in their entireties for all purposes.

BACKGROUND

Technical Field

Embodiments of the invention pertain to instantaneous feedback systems used by athletes to monitor and improve performance, and more specifically to such systems used by swimmers.

Background Information

Throughout this application, various publications, patents and published patent applications are referred to by an identifying citation. The disclosures of the publications, patents and published patent applications referenced in this application are hereby incorporated by reference into the present disclosure.

While training it is common for athletes to use devices and systems to provide themselves and their coaches with objective feedback. This is especially true for racing sports, where simple, unequivocal metrics such as time to traverse a distance, average speed, and instantaneous speed measured in training sessions correlate strongly with race performance. The value of these metrics is especially high in competitive swimming because the environmental conditions in the pool are tightly controlled. Unlike performances in other racing sports such as running, cycling, rowing, or cross country skiing, swimming performances are not affected by exogenous conditions such as wind, extreme temperature, obstructions, or interference by other competitors. This allows swimmers to meaningfully compare times recorded at different venues and lends significance to very small differences in times and speed.

Although objectively measured times and speed in the sport of swimming are among the most meaningful in all of sport, swimmers have little access to these measurements in their training sessions. In other racing sports, athletes can glance at a watch or computer mounted on their equipment without interrupting their training or racing. These watches and computers are able to present instantaneous speed information in real time derived by GPS or sport-specific devices such as a rotary encoder on the wheel for cycling or a hull-mounted impeller for rowing.

The sport of swimming is lacking both systems to collect instantaneous speed metrics in a practical manner and devices to present this information in real time to the swimmer. This lack of immediate feedback denies swimmers the most effective method to learn how subtle changes in technique can improve performance.

For most swimmers the closest metric they have to instantaneous speed is the time it takes them to swim one length of the pool or lap split. At best they have access to this metric once per lap by reading a pace clock while turning. If they are willing to go to great expense and inconvenience, motion capture or wire tether systems are available and present swimmers with a record of their instantaneous speed, but only after their performance is completed. To benefit from these measurements they must recall what they were thinking, feeling, and doing at the time speed was recorded to understand the effects of these thoughts, feeling, and actions on their speed. They cannot learn intuitively by observing the immediate effect of their actions on their speed but must learn in a contemplative manner.

But most swimmers must learn to swim faster with speed averaged over some long period such as a lap of the pool or the length of entire race as their only quantitative feedback. Variations in their speed that they might have been able to correlate to changes in technique are likely to be lost in the averaging process.

Systems and devices currently used to provide speed metrics include the following. The most common systems are listed first and provide the swimmers with only averaged speed metrics.

A pace clock is commonly used by swimmers to measure the time and speed of their swim. By observing the pace clock each lap, swimmers are able to calculate their lap split. This system is very simple, but only provides average speed information.

A coach with a stopwatch, who tells the swimmer their lap split when the swimmer is at rest. This system has the same limitations as the pace clock.

Lap counting devices that are worn by swimmers and provide information aurally after each lap is completed. Such a system is available commercially from Avidasports. This system automates the speed measurement process, but still only provides averaged information.

A system disclosed in U.S. Pat. No. 6,870,466B2 uses a proximity sensor to detect when a swimmer completes a lap and then presents this lap time or speed to the swimmer. The limitations of this method are that the speed information is averaged and the information is available after the lap is completed.

A system disclosed in U.S. Pat. No. 8,317,659B2 uses touch-sensitive devices to count elapsed lap time and provide this information to the swimmer by a display located in the pool that is visible to the swimmer while swimming. This system does not contemplate a method of providing instantaneous speed.

The following systems do provide instantaneous speed information but do so only in retrospect or in an impractical or cumbersome manner.

One approach uses a draw wire encoder attached to a swimmer, with which the swimmer's instantaneous speed is measured, and recorded. Such a system is available from Sport-Thieme. This system has the disadvantages that each swimmer must be attached to a cable, that changing direction is difficult for the swimmer, and that the cable attached to one swimmer may interfere with another swimmer's cable if multiple swimmers are using the system. Also this system does not have a means of providing immediate speed information to the swimmer.

A video motion capture system measuring instantaneous velocity is available from Qualisys AB for underwater use. The system does not have a means for providing velocity information in real time to the swimmer and requires an increasing number of cameras to track multiple swimmers.

A system using autonomous inertial sensors to calculate the position and speed of the swimmer is disclosed in U.S. Pat. No. 9,216,341B2. Currently this system is technically impractical with consumer grade inertial measurement units, since these units have a position error of greater than 25% of the distance traveled. This accuracy is not sufficient.

Improvements in speed of just a few percent represent significant progress for most swimmers. The difference in time between the winning swimmers and those not qualifying for the final is typically less than 2% in elite international events. To achieve meaningful precision using this method is economically impractical since industrial grade sensors such as Analog Devices ADIS16488 that do provide less than 1% error cost more than 1000 dollars, and one such sensor would be required for each swimmer.

A system disclosed in US 2014/0200116 A1 uses motion capture to measure the velocity of the swimmer and then relays this information to the swimmer using an FM radio. This system is substantially that of Qualisys AB with the addition of a system transmitting the data derived by motion capture to the swimmer in real time. As such, it suffers from the same scalability issues requiring evermore hardware to track more swimmers.

There are several patents in the field of swimming that disclose the use of an in-goggle display but they either do not describe how to implement such a display (U.S. Pat. No. 6,870,466B2, U.S. Pat. No. 9,216,341B2, U.S. Pat. No. 4,776,045A) or they describe a display that is impractical for swimming because of size or shape (U.S. Pat. No. 5,585,871A, U.S. Pat. No. 5,685,722A) and except for U.S. Pat. No. 9,216,341B2 and US 2014/0200116 A1 they do not disclose a method to provide instantaneous speed to the display.

The difficulty in providing an in-goggle display for swimming is reflected in the marketplace where as of 2016 Kopin and Intel are making eyewear-attached displays for cycling, running, skiing, but have yet to produce a display module for the swimming market.

Commercially available near-eye display modules are bulky and consume 60 to more than 100 milliwatts. These modules are not optimized to display the metrics most useful to swimming such as speed and splits, but rather are designed to render graphics with high pixel count. Intel makes two near-eye display products for the sports market. These products use Kopin's White Pearl module which has a volume without drive electronics of 2.9 $cm^3$ and consumes 100 milliwatts. Rechargeable batteries add another 1 $cm^3$ for every hour of battery life, so a device based on this display module with a reasonable battery life is too large to be mounted on a swim goggle. Also this module has an eye relief of 22.5 mm and it is 12.5 mm deep, so it projects 35 mm from the eye, which causes too much drag for use while swimming.

A need therefore exists for an improved swimming speedometer capable of providing real time speed information to the swimmer.

SUMMARY

In one aspect of the invention, an apparatus is provided for measuring a swimmer's speed and conveying the speed to the swimmer in real time. The apparatus includes a plurality of ultrasonic beacons each having a transducer configured to emit ultrasonic signals in a pool or other body of water within which the swimmer is swimming. A wearable, waterproof, ultrasonic receiver worn by the swimmer, receives the ultrasonic signals and generates corresponding signal data. The receiver's microcontroller captures and uses the signal data to calculate the swimmer's position and speed in real time, and conveys this information to a wearable, waterproof, user interface device worn by the swimmer, the user interface device including a near-eye display disposed on the swimmer's googles.

In another aspect of the invention, a method of measuring a swimmer's speed and conveying the speed to the swimmer in real time, includes deploying a plurality of ultrasonic beacons each having an ultrasonic transducer, to emit ultrasonic signals in a body of water within which the swimmer is swimming. The method further includes receiving, with a wearable, waterproof, ultrasonic receiver worn by the swimmer, the ultrasonic signals emitted by the beacons and generating corresponding signal data. The receiver's microcontroller captures and uses the signal data to calculate the swimmer's position and speed in real time, and conveys this information to the user via a wearable, waterproof, user interface worn by the swimmer, using one or more of visual, audible, and tactile output, the user interface device including a near-eye display configured for being disposed on swim googles worn by the swimmer.

In yet another aspect of the invention, a method of producing an apparatus for measuring a swimmer's speed and conveying the speed to the swimmer in real time, includes configuring a plurality of ultrasonic beacons each having an ultrasonic transducer, to emit ultrasonic signals in a body of water within which the swimmer is swimming. The method further includes configuring a wearable, waterproof, ultrasonic receiver for being worn by the swimmer, to receive the ultrasonic signals emitted by the beacons, and to generate corresponding signal data. The receiver's microcontroller is configured to capture and use the signal data to calculate the swimmer's position and speed in real time. A wearable, waterproof, user interface device is configured for being worn by the swimmer, and to convey the swimmer's speed to the swimmer in real time, using one or more of visual, audible, and tactile output, wherein the user interface device includes a near-eye display configured for being disposed on swim googles worn by the swimmer.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

Embodiments of the present invention are illustrated by way of example and not limitation in the figures of the accompanying drawings, in which like references indicate similar elements and in which.

DETAILED DESCRIPTION

Figure 1:
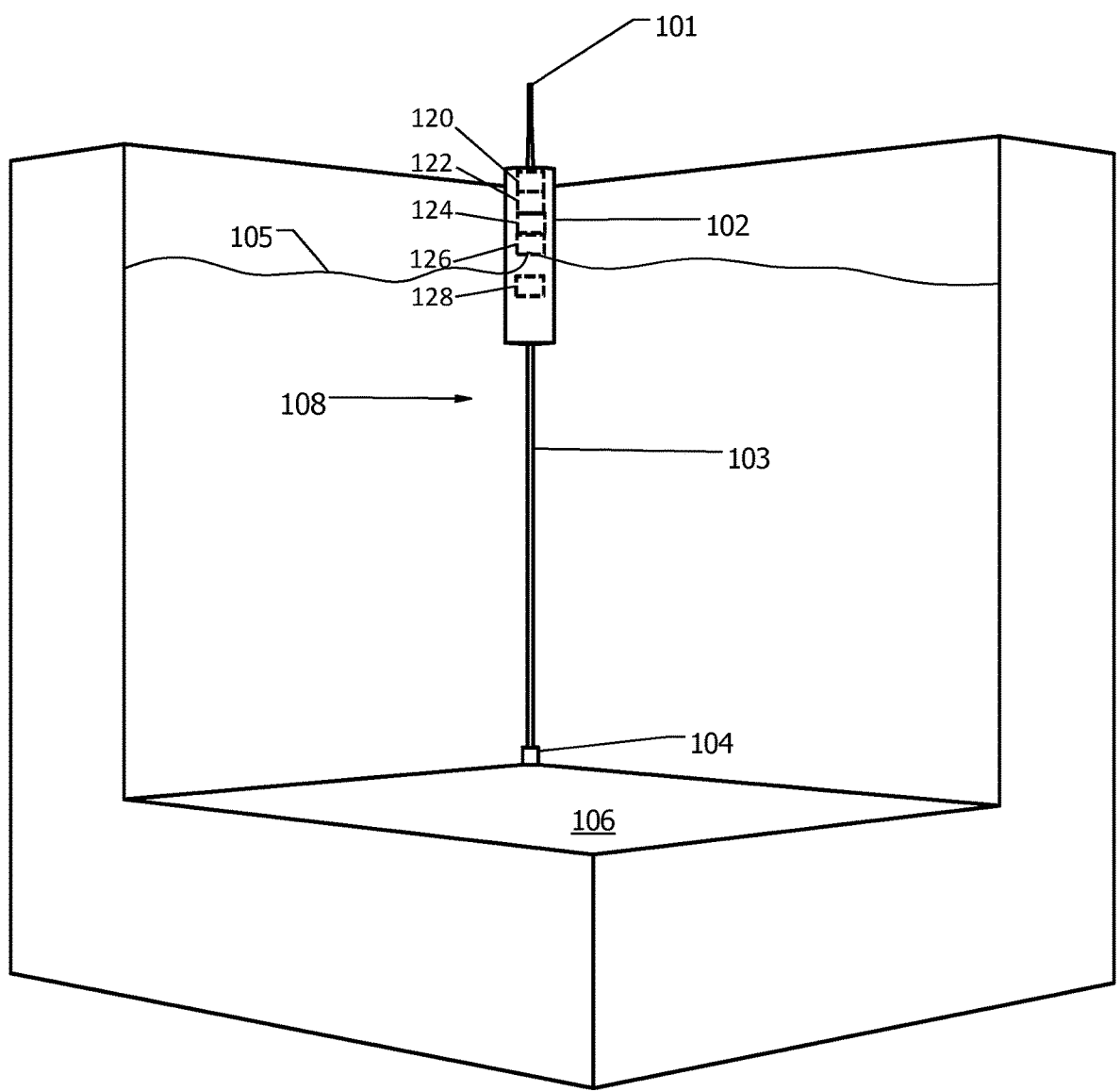
FIG. 1 is a perspective view of a beacon component of an embodiment of the invention, with interior portions shown in phantom, installed in a corner of a swimming pool.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. In addition, well-known structures, circuits and techniques have not been shown in detail in order not to obscure the understanding of this description. The following detailed description is, therefore, not to be taken in a limiting sense, and the scope of the present invention is defined by the appended claims and their equivalents.

As used in the specification and in the appended claims, the singular forms "a", "an", and "the" include plural referents unless the context clearly indicates otherwise. For example, reference to "an analyzer" includes a plurality of such analyzers. In another example, reference to "an analysis" includes a plurality of such analyses.

Although specific terms are employed herein, they are used in a generic and descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

General Overview

Embodiments of the invention overcome disadvantages in the prior art identified in the Background. Specifically, it provides immediate, precise instantaneous speed and timing information to the swimmer using a system that is easily scalable to multiple simultaneous users.

Embodiments of the invention include multiple ultrasonic beacons immersed in the pool at fixed, known locations and a receiver and display worn by each swimmer in the pool. As will be discussed in greater detail hereinbelow, these embodiments operate in a manner generally analogous to the Global Positioning System (GPS), e.g., using trilateration, but do so using ultrasonic, rather than radio frequency emissions. These embodiments also address various difficulties associated with the use of ultrasonic, rather than radio frequency, signals.

Each beacon emits uniquely identifiable ultrasonic pulses at predetermined times. The receiver worn by swimmers in the pool detects these pulses and records the time of detection. The receiver then calculates its position and velocity based on the time of pulse detection, the known position of the beacons, and the Doppler shift of the pulse frequency. In these embodiments, the beacons are analogous to the GPS satellite constellation and the receiver is analogous a GPS receiver. The ultrasonic pulses are analogous to the radio transmissions from the satellites to the GPS receivers. These embodiments can support a substantially unlimited number of users, since each receiver is passive and does not interfere with the operation of other receivers.

This beacon-receiver combination addresses the problem of scalability of instantaneous speed measurement. It also addresses the problem of economic feasibility as discussed hereinabove with respect to U.S. Pat. No. 9,216,341. Unlike such inertial systems, which would require each swimmer to wear a relatively expensive (e.g., $1,000) inertial measurement unit to receive reasonably precise speed information, these embodiments simply require a small number (e.g., four) of beacons per pool, each with a relatively inexpensive (e.g., $100) transducer and an inexpensive (e.g., $15) ultrasonic receiver worn by each swimmer. So, as the number of swimmers increases, the per-user transducer plus receiver cost is less than $1/50^{th}$ the per swimmer cost of inertial sensors at today's prices.

Notably, these embodiments also provide immediate, i.e., real time, feedback to the swimmer, a functionality lacking in the other approaches discussed hereinabove. The beacon-receiver combination allows the receiver carried by the swimmer to calculate the instantaneous speed.

A component of these embodiments, the display unit, receives the calculated speed from the receiver either through a wired or wireless connection and presents this information to the swimmer as text. The display is attached to or integrated into the swim goggle, and thus is visible to the swimmer without their having to interrupt their swimming motion.

Unlike patents in the field of swimming that mention in-goggle displays (U.S. Pat. No. 6,870,466B2, U.S. Pat. No. 9,216,341B2, U.S. Pat. No. 4,776,045A, U.S. Pat. No. 5,585,871A, U.S. Pat. No. 5,685,722A) but present either no details of their implementation or an implementation that is not practical for swimming, embodiments of this invention disclose a goggle mounted display unit that is practical for swimming. In particular embodiments, the instant display, including battery and drive electronics, has a volume of less than 3 $cm^3$ and can be mounted very close to the eye on the surface of the goggle so it is streamlined for swimming. By using a novel, low pixel count passive matrix display that is optimized for displaying text such as speed and splits, in particular embodiments, the display system of the present invention consumes less than 300 microwatts of power.

Terminology

For the purposes of the present specification, the term "computer" is meant to encompass a workstation, personal computer, personal digital assistant (PDA), wireless telephone, or any other suitable computing device including a processor, a computer readable medium upon which computer readable program code (including instructions and/or data) may be disposed, and a user interface. The term "microcontroller" is used in its conventional sense, to refer to a small computer (SoC) on a single integrated circuit containing a processor core, memory, and programmable input/output peripherals. The term "real-time" refers to sensing and responding to external events nearly simultaneously (e.g., within milliseconds or microseconds) with their occurrence, or without intentional delay, given the processing limitations of the system and the time required to accurately respond to the inputs. Terms such as "component," "module", and the like are intended to refer to a computer-related entity, either hardware, a combination of hardware and software, or software in execution. One or more components may reside within a process and/or thread of execution and a component may be localized on one computer and/or distributed between two or more computers or control devices.

Programming Languages

The system and method embodying the present invention can be programmed in any suitable language and technology, such as, but not limited to: Assembly Languages, C, C++; Visual Basic; Java; VBScript; Jscript; Node.js; BCMAscript; DHTM1; XML and CGI. Alternative versions may be developed using other programming languages including, Hypertext Markup Language (HTML), Active ServerPages (ASP) and Javascript. Any suitable database technology can be employed, such as, but not limited to, Microsoft SQL Server or IBM AS 400.

Referring now to the Figures, embodiments of the present invention will be more thoroughly described.

System Components

Embodiments of the invention have three primary components. The first component is a set of multiple beacons that provide navigational signals usable by any swimmers in the pool in accordance with the teachings hereof. This component is therefore a resource shared by all such swimmers. The second component is a receiver that each swimmer wears. This receiver decodes the navigational signals from the beacons and calculates the swimmers position and speed. The third component is a display unit worn by the swimmer that conveys this speed and position in real time to the swimmer. Aspects of these three components are listed and described below.

Figure 2:
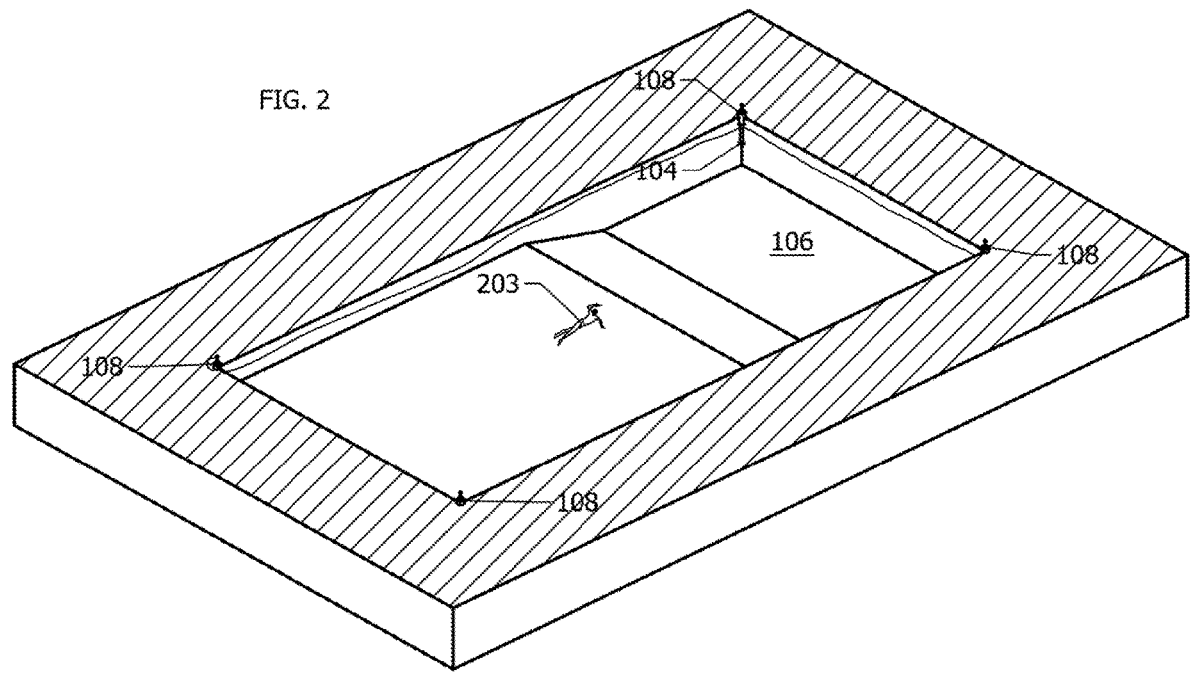
FIG. 2 is a perspective view of a pool with beacons installed and a swimmer using the embodiment of FIG. 1.
Figure 3:
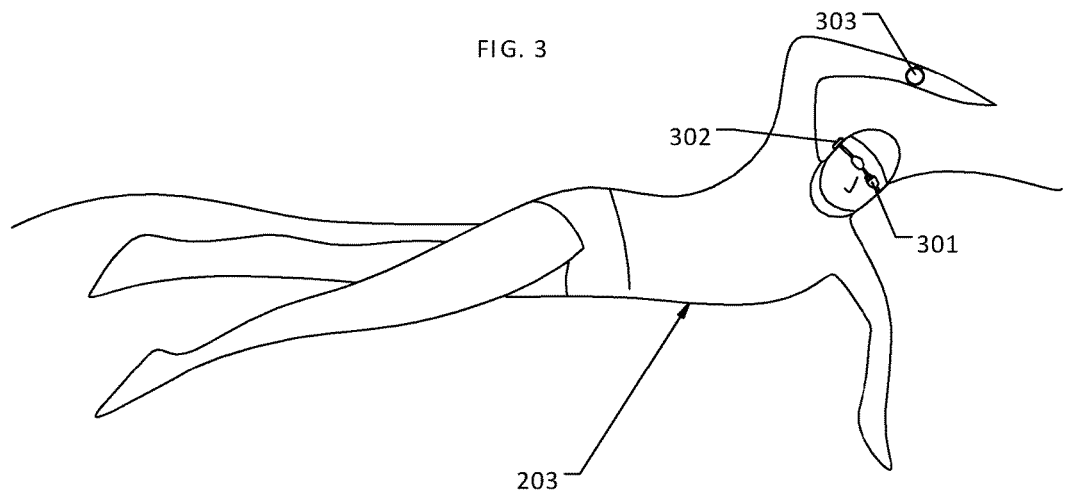
FIG. 3 is a schematic view of a swimmer wearing a receiver and display unit of an embodiment of the present invention.

As shown in FIGS. 1-3, multiple beacons 108 are partially immersed in the swimming pool at fixed locations, a receiver that detects navigational signals transmitted by the beacons and is worn on the head 302, the wrist 303, or any portion of the body of the swimmer 203 that is immersed in water during each swim stroke, and a display system 301 worn by the swimmer analyzes the navigational signals transmitted by the beacons 108 and presents them to the swimmer in a meaningful way.

In particular embodiments, the beacons each include a radio 102 in a waterproof housing, with antenna 101, and an ultrasonic piezoelectric transducer 104 with associated drive circuitry and an optional pressure sensor, communicably coupled to the radio 102 via an adjustable length conduit 103. Embodiments of radio 102 include within its housing, a microcontroller 120, a clock 122, a power source such as battery 124, a salinity sensor 126, and a temperature sensor 128, as shown in phantom.

Embodiments of the receiver 302, 303 worn by the swimmer include an ultrasonic piezoelectric receiver, a microcontroller, a battery, a radio, and a capacitive sensor and/or accelerometer or other means for automatically waking the receiver from a sleep state. In some embodiments, the receiver 302, 303 is disposed remotely from the display unit 301, such as shown in FIG. 3. However, in other embodiments, such as shown and described with respect to FIGS. 6-12, the receiver is disposed integrally with the display unit 301 located on the goggles worn by the swimmer. As best shown in FIG. 10, a receiver of this integrated embodiment includes a microcontroller 1010, an optical display 1103 (FIG. 12), a battery 1001, a radio 1012, and sensors that may include the accelerometer 1014, a pressure sensor 1016, a capacitive sensor 1018, and piezoelectric receiver 1020. It should be noted that the inclusion of a pressure transducer in the receiver is not required for typical swim training (surface swimming) applications. However, use of a pressure sensor in the receiver may be desirable for use in diving applications, to provide vertical positioning precision. The inventor has recognized that since conventional swimming pools are much longer and wider than they are deep, the inclination (i.e., angle relative to the horizontal) of a line connecting any transducer to the receiver is small. This creates a relatively large vertical dilution of precision (VDOP). In typical swim training the swimmer is near the surface of the water and only their horizontal position and speed are of interest, so poor vertical precision is not a significant concern. If, however, vertical position is important as it might be for a diver, then a pressure transducer would be useful to help mitigate the aforementioned VDOP.

Operation

1. Placement of the Beacons

Before the display unit can provide instantaneous speed information to the swimmer, the beacons must be placed in the pool and synchronized/calibrated. The beacons 108 would typically be placed in the four corners of the pool as indicated in FIGS. 1 & 2. Additional beacons may be placed to provide additional signals, e.g., to provide redundancy and/or improved accuracy. As shown in FIG. 1, the top of each beacon protrudes above the surface of the water and supports an antenna 101 for the radio. The piezoelectric transducer 104 is located near the bottom of the pool 106 and is positioned by adjusting the length of conduit 103 connecting it to the radio 102. An optimum depth for the piezoelectric transducer 104 is the greatest depth that gives the transducer a line-of-sight to all points on the surface of the pool. This placement of the piezoelectric transducer helps to minimize multipath interference and provide an unobstructed path between the transducer 104 and the receiver 302, 303 worn by the swimmer. This placement also helps minimize the position dilution of precision.

2. Self-Calibration/Synchronization of the Beacons

Figure 4:
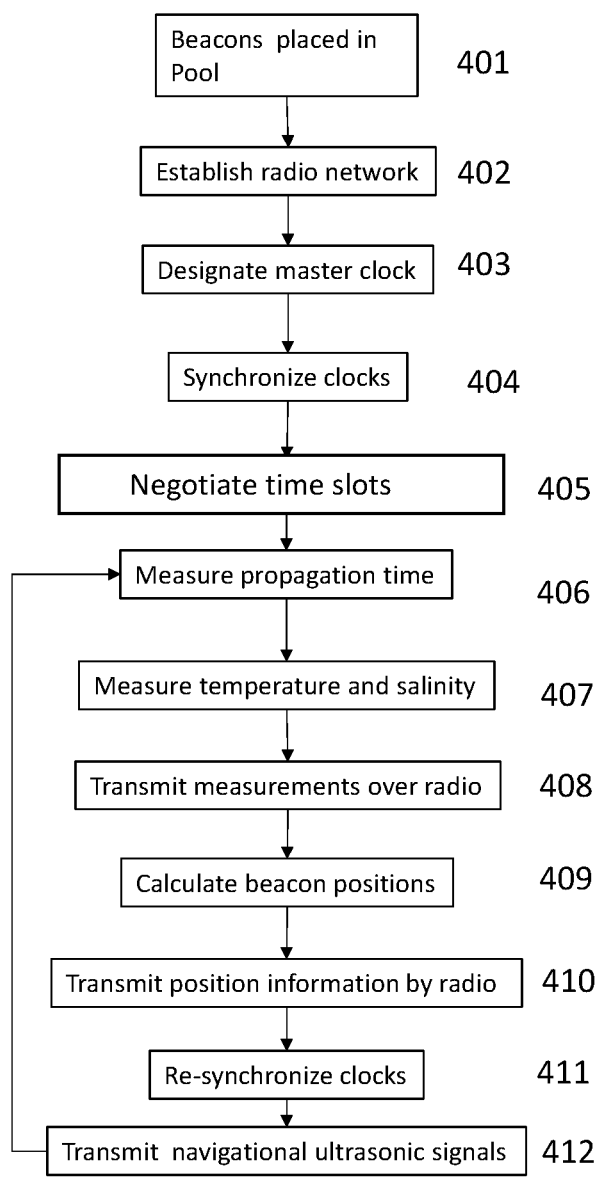
FIG. 4 is a flowchart of a beacon calibration process in accordance with embodiments of the present invention.

The calibration process is outlined in FIG. 4. After the beacons are placed in the pool at 401, they then begin calibrating themselves. The beacons establish a conventional star network using their radios 402. This may be achieved using Wi-Fi, Bluetooth LE, or other protocol that allows reliable communication over an approximately 60 meter range. The beacons use this network to synchronize their clocks. One of the beacons is designated to serve as the hub of the network and its clock is designated as the master clock 403. The hub beacon then broadcasts a clock-reset signal that instructs all other beacons to reset their clocks to a specific time. This synchronization 404 does not need to be extremely precise since the speed of sound in water is 1500 m/s. To achieve one centimeter positioning precision requires the clock of each beacon to be synchronized within 6.66 microseconds. Clock synchronization does not require compensation for the distance between beacons since radio propagation delay will be less than 167 nanoseconds for beacons less than 56 meters apart, the diagonal distance between corners of a 50 meter by 25 meter pool. A method used by the beacons to calculate their position is described in the following paragraph. Since the radio propagation delay between beacons is not significant, the beacons can calculate their relative position to sufficient precision without external assistance.

Once the clocks are synchronized 404, the beacons may negotiate by radio, time slots for each beacon to transmit ultrasonic signals 405. The beacons will transmit their ultrasonic signals at mutually distinct frequencies and/or using any number of conventional modulation schemes that allow their transmissions to be distinguished from those of the other beacons. Each beacon will capture the arrival of ultrasonic signals transmitted by other beacons using its transducer 104. Each beacon will then use its microcontroller 120 and clock 122, to record the time of arrival of those ultrasonic signals and compare those times of arrival to the negotiated transmission time to calculate the ultrasonic signal propagation time 406 through the water. In particular embodiments, the microcontroller 120 of each beacon will also capture and record the depth of its transducer, its local temperature, and local salinity 407 and share by radio the measured ultrasonic signal propagation times, depth, temperature, and salinity with the other beacons 408. In particular embodiments, the transducer depth is determined by a pressure sensor that is co-located with, or located at a predetermined depth relative to, the piezoelectric transducer 104.

The beacons then convert the ultrasonic signal propagation times to distance using the measured temperature, salinity, depth, and the following formula (Medwin H, 1975 Speed of sound in water: A simple equation for realistic parameters Journal of the Acoustical Society of America, 58, 1318-1319, 1975):

$$\frac{D}{t} = c = 1449.2 + 4.6T - 5.5 \times 10^{-2}T^2 +$$
$$2.9 \times 10^{-4}T^3 + (1.34 - 10^{-2}T)(S - 35) + 1.6 \times 10^{-2}$$

Where
t is propagation time in seconds
D is distance in meters
c is the speed of sound in m/s
T is temperature in ° C.
S is salinity in ppt
z is depth in meters.

The distances between transducers 104, along with the depths provided by their associated pressure transducers, fully determine the position of the transducers. For each transducer pair a,b the relation between their location coordinates (x,y,z) and distance D is determined by the following formula.

$$D_{a,b} = \sqrt{(x_a - x_b)^2 + (y_a - y_b)^2 + (z_a - z_b)^2}$$

This provides six equations. There are 12 coordinates necessary to determine the location of all the transducers. The horizontal coordinates x, y of one transducer can be set to zero, since only relative position is important, and the depths, z, of each transducer are determined by its associated pressure transducer. This leaves six unknown coordinates and six equations, so the (x,y,z) position of each beacon can be determined 409. Each beacon transmits by radio every beacons' position, temperature, and salinity using its radio 410. Additionally, as mentioned above, each beacon transmits by radio the predetermined schedule by which it will transmit its ultrasonic navigational signals, as negotiated at 405.

The beacons may now re-synchronize their clocks 411 and begin to transmit ultrasonic navigational signals that allow receivers worn by swimmers in the pool to determine their position and speed 412.

As mentioned, each beacon stores its (x,y,z) position information and in particular embodiments, is configured to periodically recalculate its position to ensure the validity of the position information. To facilitate these calculations, and to maintain the accuracy of the swimmer's speed measurements as discussed hereinbelow, the beacons will periodically re-synchronize their clocks 411, e.g., on the order of once per second if they use a precision, low cost clock such as the Maxim DS32kHz TXCO (Temperature Compensated Crystal Oscillator) available from Maxim Integrated (San Jose, Calif.) which has a frequency stability of ±2 ppm. This information will be broadcast by the beacons' radios and encoded in the ultrasonic navigational signals transmitted by the beacons.

The beacons would normally be permanently fixed in the pool and have long-lived, hot-swappable batteries. Thus, the beacons would normally be synchronized, calibrated, and transmitting navigational signals continuously during operation after their initial installation. It should be recognized, however, that the beacons may be portable and removably installed, e.g., for temporary use in various pools or other swimming venues. In this regard, although embodiments of the present invention are shown and described as being used in swimming pools, other suitable swimming venues include outdoor locations such as freshwater ponds/lakes and larger salt water venues. Where embodiments of the present invention are used outdoors, the radio 102 may include a GPS receiver. The beacons' clocks may be synchronized and horizontal positions may be determined using GPS receivers alone or using GPS receivers to assist the above-described self-calibration and synchronization method.

3. Receiver Operation

Figure 5:
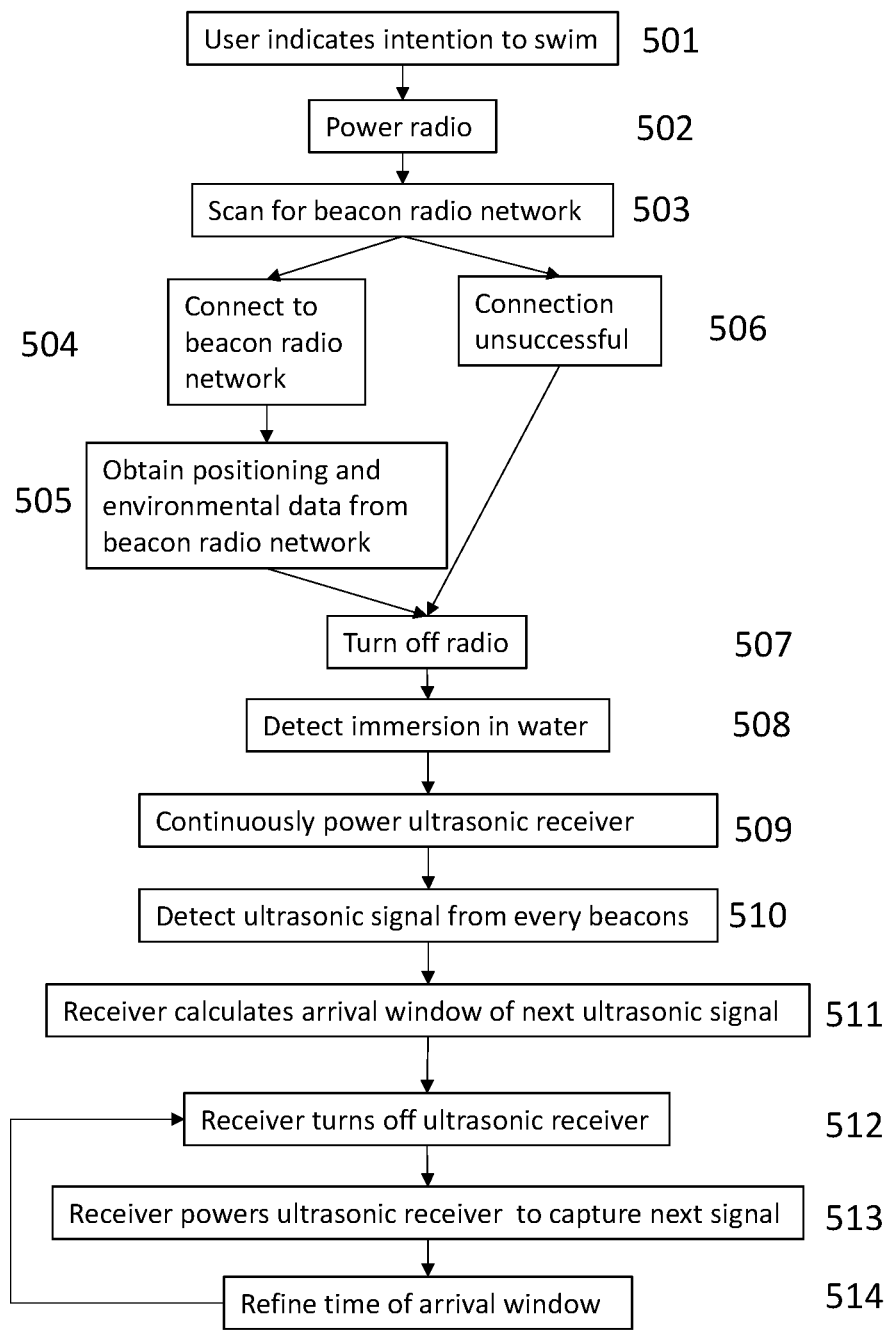
FIG. 5 is a flowchart of a receiver initialization and calibration process in accordance with embodiments of the present invention.

Turning now to FIG. 5, the receiver 302, 303 (FIG. 3) initializes itself at the start of each swim. In particular embodiments, when the receiver's accelerometer detects a tap from the swimmer 501, indicating their intention to begin using the system, or alternatively, the receiver's capacitive sensor detects contact with water, the receiver will transition from a hibernation state to a ready state and turn on its radio 502 and scan for the beacon network 503. If the receiver successfully connects to the beacon network 504, it will receive the above-described beacon positioning data, temperature, salinity, and clock data 505 and then turn off its radio 507, e.g., to conserve power, while the receiver remains in its ready state. If the receiver fails to make a radio connection with the beacon network 506 after a predetermined period, it will turn off its radio, while the receiver remains in its ready state. It should be noted that while it is convenient, and in some applications, desirable to obtain the beacons' positioning, temperature, salinity, and clock data via the beacon's radio network, as discussed hereinabove, in particular embodiments this data is also encoded into the beacons' ultrasonic navigational signals. Therefore, if the radio connection was unsuccessful, the receiver will be able to acquire this data from the ultrasonic navigational signals once it is in the water.

In particular embodiments, as mentioned above, the ultrasonic signal data captured by the receiver includes time of arrival of the ultrasonic signals as well as location information for the beacon originating each of the ultrasonic signals. The receiver's microcontroller is configured to use the signal data and time of origin information for the ultrasonic signals to determine distance between the swimmer and each of the beacons in real time, using the formula:

$$D = ct$$

where
t is propagation time in seconds
D is distance in meters
c is the speed of sound in m/s The speed of sound is determined by the beacons as described above and encoded in the beacons' navigation signals. The microcontroller may then use the distance between the receiver and each of the beacons to determine the location of the receiver (xa,ya,za) using the formula $$D_{a,b} = \sqrt{(x_a-x_b)^2+(y_a-y_b)^2+(z_a-z_b)^2}.$$

where Da,b is the distance between each the receiver (a) and each beacon (b), and (xb,yb,zb) is the location of beacon (b).

When the receiver determines that it is in the water 508 using its capacitive sensor and/or accelerometer as discussed hereinabove, it will turn on its piezoelectric detector. Alternatively, rather than this automatic activation, the receiver may be configured to be turned on manually, e.g., with a waterproof switch. When the receiver is first in the water it does not know its location relative to the beacons. It must power its receiver circuitry and listen continuously 509 for navigational signals transmitted by the beacons. To minimize power consumption, in particular embodiments, once the receiver has detected a signal from all beacons 510, it may calculate a the time window within which the next signal is anticipated to arrive 511 and turn off its piezoelectric sensor and receiver circuitry 512 until that time window opens. The receiver calculates the the time window's length, which is determined by the uncertainty in the velocity of the swimmer.

Initially the receiver does not know the velocity of the swimmer, but this velocity will always be less than 5 m/s, so the uncertainty in time of arrival will be $$t_{uncertainty} = \pm \frac{5 \times t_{interval}}{c}.$$

$t_{interval}$ will be less than 100 ms, in order to provide accurate, per-stroke speed information to the swimmer. Thus $t_{uncertainty} = \pm 330$ μs. This will be the listening window once all the beacon navigational signals are detected, but before the receiver has any knowledge of its velocity.

Once the receiver has received more than two consecutive signals from each beacon it can calculate its radial velocity relative to each beacon based on the change in $t_{interval}$ between successive signals for each beacon. The receiver may also calculate its radial velocity based of the Doppler frequency shift of the beacon signals.

The radial velocities at time $t_n$ can be used to better the estimate the time of signal arrival at time $t_{n+1} = t_n + t_{interval}$ 514. The uncertainty in this estimate is $$t_{uncertainty} = t_{interval} \times v_{uncertainty} + \frac{1}{2c} a t_{interval}^2$$

where $v_{uncertainty}$ is the uncertainty in the measured velocity, α is the maximum possible acceleration. Based on collected data, α is less than 20 m/s² and $v_{uncertainty}$ should be less than 1% of velocity, or 0.02 m/s. During normal operation $t_{uncertainty} = \pm 68$ μs. This will be the listening window during normal operation.

In order to reduce the measured time of arrival of the navigational signals to accurate position and speed, the receiver must know the position of the beacons and be able to calculate the speed sound in the pool. As discussed hereinabove, this information is either acquired from the beacon radio network or from the data encoded in the navigational signals.

Whenever the swimmer leaves the pool and re-enters, 509 through 514 of the acquisition process may be repeated. In this regard, the receiver may power down its ultrasonic receiver after a predetermined period of failure to detect ultrasonic signals, which may be interpreted as the receiver being no longer submerged. Particular embodiments may allow for periods of time in which the swimmer is resting between swims in a position where the receiver is not submerged, by increasing the listening window as a function of the time not submerged in order to facilitate reacquisition of the beacon signals when the receiver is re-submerged.

Once the receiver has acquired the beacon signals and has calculated its speed based on the time of arrival of the beacon signals or Doppler frequency shift of the signals, the receiver will relay this speed to the display unit 301. This information can be relayed by ultrasonic signals like those used for navigation when both the display and receiver are immersed, or by radio if the receiver and display are in close proximity such as when the receiver is worn on the head 302. In particular embodiments, the display unit 301 uses its accelerometer to update the speed presented to the swimmer at regular intervals, normally once per stroke.

Ultrasonic Signals

As mentioned hereinabove, in particular embodiments, the ultrasonic navigational signals are modulated with beacon positioning data, temperature, salinity, and clock data so that the receiver can calculate its position and speed without other external information. The navigational signals transmitted from the beacons to the receiver are generated and detected by conventional piezoelectric transducers, which those skilled in the art will recognize convert electrical signals to mechanical vibrations and mechanical vibrations to electrical signals. The electrical signals produced by the transducers are substantially identical to those generated by the antenna in radio communications. A simple method to detect and demodulate the electrical signal produced by the receiver's piezoelectric transducer is to use a frequency modulation intermediate frequency integrated circuit such as New Japan Radio Co.'s NJM2294 to detect and decode a frequency shift keying (FSK) signal. The baseband frequency of the ultrasonic signal is within the IF range of the NJM2294 and can be directly demodulated by the NJM2294. One skilled in the art of radio design will understand that many other modulation and demodulation techniques and circuitry can be applied to the electrical input and output of the piezoelectric transducer.

Regardless of the electronic modulation and detection methods, the resultant ultrasonic signals must travel from the beacon to the receiver and be detectable at the receiver. The present inventor has recognized that conventional swimming pools create a highly reflective acoustic environment, which presents some challenges for embodiments of the invention. For example, the air-water interface is nearly perfectly acoustically reflective and the walls of the pool, usually made of a cementitious material, are highly reflective. The acoustic impedance of water is $1.5 \times 10^6$ rayls while that of concrete is typically 7–10×10⁶ rayls. (See, e.g., Nawy, Edward G. Concrete Construction Engineering Handbook, § 21-32, CRC Press, Jun. 24, 2008.) This impedance mismatch and the greater speed of sound in concrete indicates a reflection coefficient of 0.68 to 1, depending on the angle of incidence, at the water-concrete interface. Any signals introduced into the pool will reverberate and could be mistakenly detected at the receiver as the direct-path signal. To mitigate the effect of these reflections, embodiments of the invention may employ three strategies are employed. the beacon signals are very brief, preferably less than 100 µs. the time interval between beacon signals is as long as possible while still providing non-aliased speed measurements for the swimmer. This time interval is preferably 100 ms. These two strategies minimize the total acoustic energy in the pool and hence the noise at the transmission frequencies in the pool. A still further strategy is to choose the frequencies of the beacon signals so that they substantially attenuate during the time interval between beacon signals.

Figure 13:
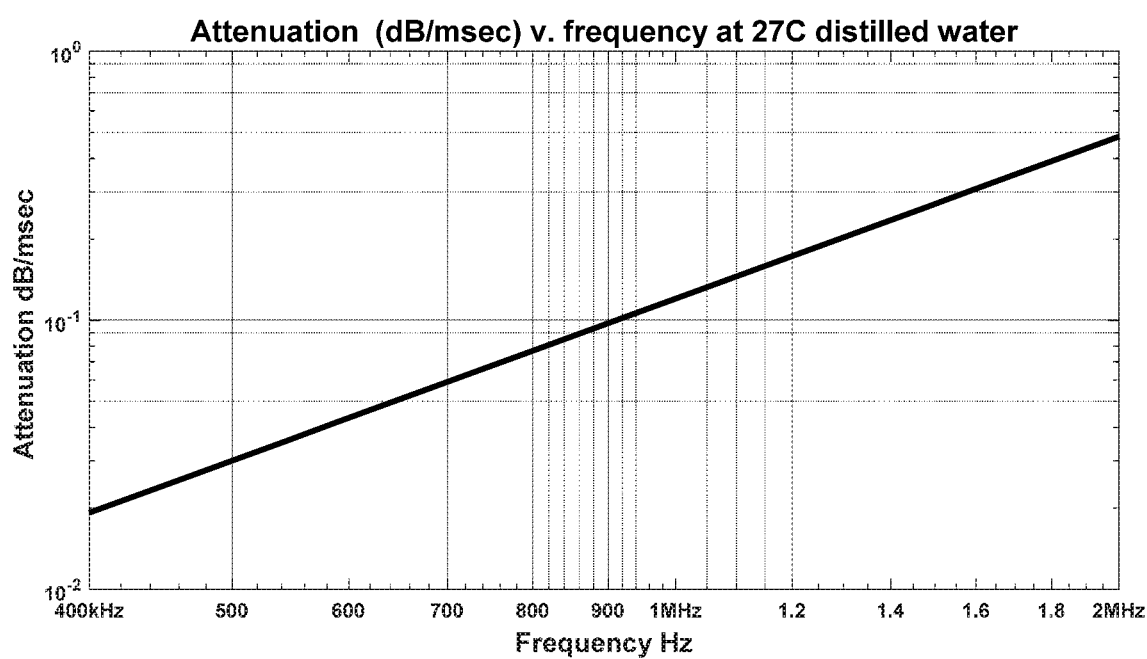
FIG. 13 is a graph showing the attenuation of sound in water.

FIG. 13 shows the relation between frequency and attenuation rate for sound in water. A desirable frequency for ultrasonic navigational signals is between 800 kHz and 2.0 MHz, to help prevent interference from the navigational signal transmitted during the previous time interval. This choice of frequency is intended to address potential interference from previous signals at the receiver when the receiver is most distant from a beacon. When a receiver is near a beacon, the intensity of the direct navigational signal is much greater than that of any reflection of the previous time interval's signal because of the large ratio of spherical spreading, which tends to minimize interference. However, when the receiver is most distant from the beacon, e.g., 56 meters in a 25 meter by 50 meter pool, the ratio of the intensity of the current signal to that of the previous time interval's signal could be as little as $$-20\log\frac{56\text{ m}}{150\text{ m}} = 8.55\text{ dB}$$

for signals transmitted at less than 400 kHz. The inventor has recognized that by using a frequency between 800 kHz and 2.0 MHz, an additional 8 to 50 dB of attenuation of the previous interval's signal can be achieved.

The inventor has also recognized that if even higher frequencies are chosen, the navigational signals will not have sufficient intensity when they arrive at the receiver. In particular embodiments, the intensity of the beacon navigational signal is limited to about 5 W/m² at the transducer by cavitation and the practical size of the transducer is limited to about 3 cm². This limits the navigational signal intensity to 192 dB relative to 1 µPa at 1 meter from the beacon and 157 dB at 56 meters assuming no frequency dependent attenuation. At 2.0 MHz there is 17 dB of frequency dependent attenuation, and the intensity at the distant receiver is at most 140 dB. At 3 MHz there would be 38 dB of frequency dependent attenuation.

A typical receiver will have acoustic performance similar to the Teledyne RESON T4038 hydrophone. The inherent noise density of this transducer is 80 dB per √Hz so the noise in a 50 kHz band would be 126 dB, giving a signal to noise ratio of 14 dB for a 2.0 MHz signal transmitted at maximum intensity. For the same signal to noise ratio, a 3 MHz signal may only have a bandwidth of 0.3 kHz. The maximum bit rate is approximately twice the bandwidth, so a 3 MHz signal would have difficulty transmitting the beacon positioning data, temperature, salinity, and clock data in a 100 µs window.

Another advantage of transmitting the navigational signals at a frequency greater than 800 kHz is the wavelength of these signals, less than 1.9 millimeters, is small compared to the scale of roughness of most pool surfaces. This means there will be limited specular reflection from the pool walls and bottom and reduced multipath interference at these frequencies versus lower frequencies.

As mentioned above, the inventor has also recognized that the navigational signal from each beacon must be uniquely identifiable. This may be achieved in many ways. One method is to assign a unique frequency to each beacon. Another method is to modulate each beacon signal with a unique code. One skilled in the art of radio communication would be familiar with these and many other multiple access channel sharing methods.

As described in the beacon synchronization and calibration process, each beacon calculates and stores the position of all beacons upon power up and periodically recalculates their positions and remeasures the temperature and salinity to calculate the speed of sound in the pool. This position and sound speed information maintained by the beacons is transmitted to the receiver worn by the swimmer so that the receiver can calculate its position using substantially the same method that the beacons used to calculate their positions during calibration. This information is transmitted from the beacon to the receiver by modulating the ultrasonic navigational signal using FSK (frequency-shift keying) or other modulation scheme known to those skilled in the art of radio communication.

In representative embodiments, the receiver must receive 161 bits of information from the beacons to calculate its position with no loss of accuracy due to quantization error. These bits may be allocated as follows.

Sixteen (16) bits are used for each component of the horizontal position of three of the four beacon transducers. The horizontal components of the location of one of the beacons can be assumed to be zero. Thirteen (13) bits are used for the vertical component of the position of all four beacon transducers.

This allocation of bits allows a horizontal position of 0 to 65.5 meters and a vertical position of 0 to 8.2 meters to be specified to one millimeter precision. This spans a volume that is larger than almost all swimming pools. Millimeter precision is sufficient to preserve accuracy since the temperature dependence in the speed of sound will introduce errors greater than 10 millimeters over a 50 meter distance. Thirteen (13) bits are used to encode the speed of sound. This is sufficient precision since temperature inhomogeneities on the order of 0.1° C. will introduce errors on the order of 1 part in 4500. Four (4) bits of the 161 bits are transmitted by each of 4 beacons at 100 ms intervals using a 100 µs long transmission. This allows the entire 161 bits to be transmitted in one second, at a bit rate that is easily supported by the previously described 2 MHz navigational signals.

Display System

3. Display of Speed

As also mentioned above, embodiments of the invention use an in-goggle display system 301 (FIGS. 3, 6-8). This allows the instantaneous speed data determined by the receiver to be presented to the swimmer in real time so that this data can be best used to improve the swimmer's performance. Unlike other potential in-goggle display approaches for providing swimming feedback, the instant embodiments provide a practical implementation.

Figure 12:
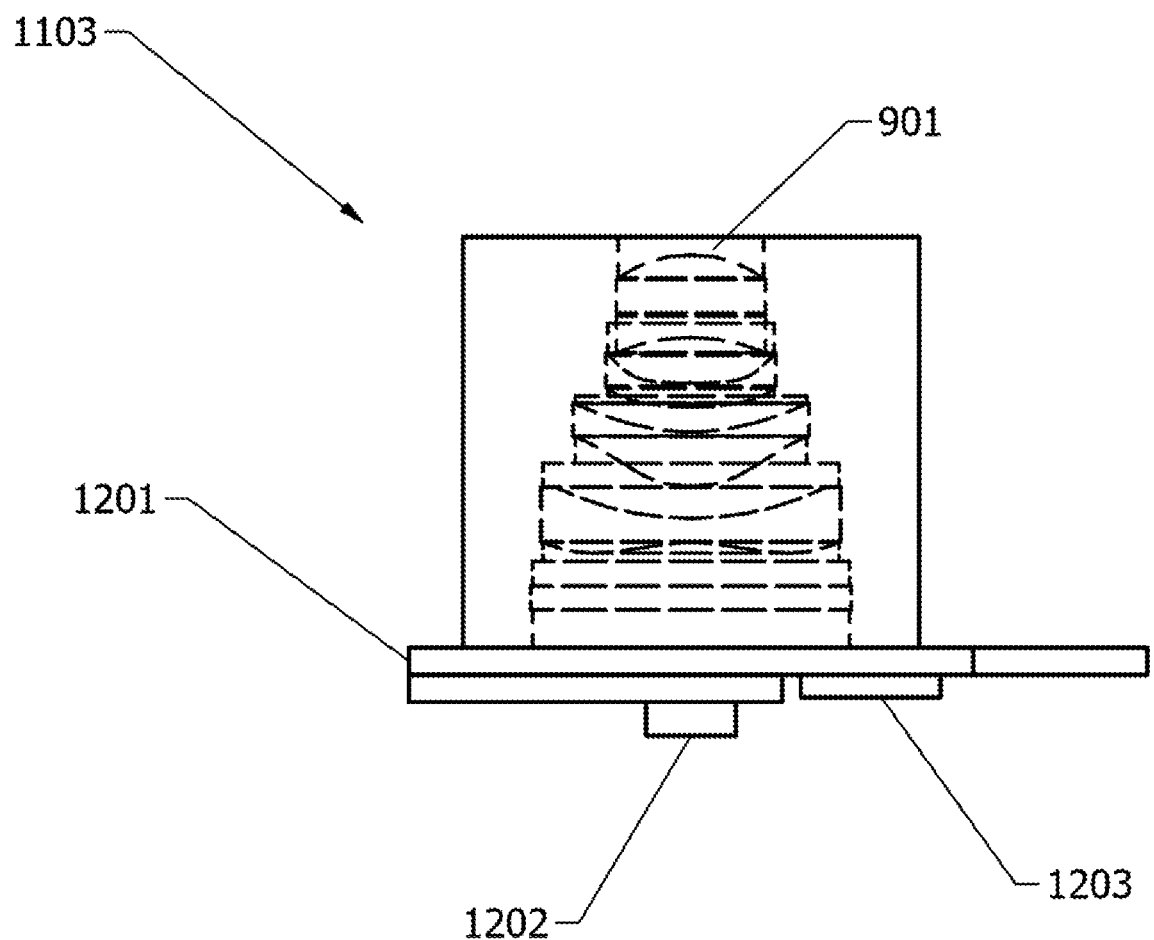
FIG. 12 is an elevation view, with internal components shown in phantom, of optical components of the display unit of FIGS. 6-11.

Turning now to FIG. 12., an optical display module 1103 contained in the display unit 301 is shown. In the exemplary embodiment shown, the components of the optical display module 1103 include an LED 1202, model CREE XQEGRN-H2-0000-000000B01, with a 980 µm×980 µm die, a passive STN LCD 1201 composed of a liquid crystal material sandwiched between two layers of 0.3 mm thick glass patterned with indium tin oxide (ITO) row and column electrodes on a 10 µm pitch, and a lens 901, Largan model 9498, with an effective focal length (EFL) of 4.2 mm. The LCD's construction is that of a conventional passive STN display except its electrode pitch is much smaller than that of a conventional display.

This LCD 1201 is driven by an EM Microelectronic EM6127 controller 1203. The active area of the LCD where the image is generated is 1010 µm×320 µm (101×32 pixels). The size of the active area of the display is important because the ratio of the width of the active area to the EFL determines the field of view (FOV) of the display, specifically $FOV=2\times\tan^{-1}$ (width of active area/(2×EFL)). The FOV should be less than 15 degrees so text can be read without scanning across the display image. It is desirable to have the EFL be as short as possible to make the display as thin as possible. Lenses are available with very short EFL's, so it is the width of the active area that determines the overall thickness of the optical display module 1103.

Figure 6:
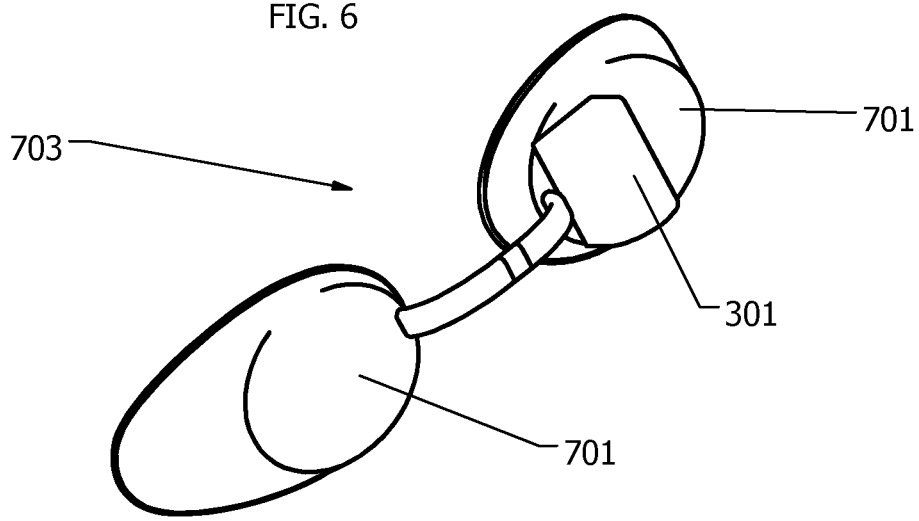
FIG. 6 is a perspective view of a display unit of the invention mounted to goggles.
Figure 7:
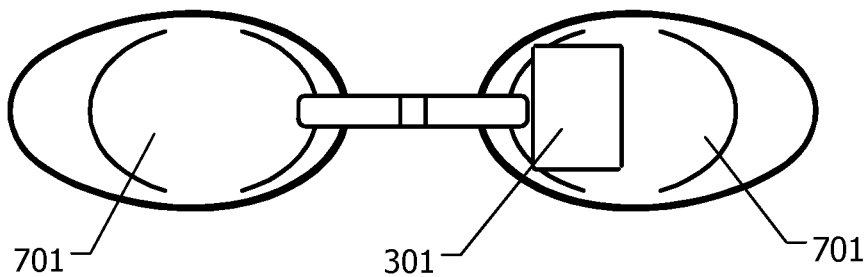
FIG. 7 is a front elevation view of the display unit of FIG. 6 mounted to goggles.
Figure 8:
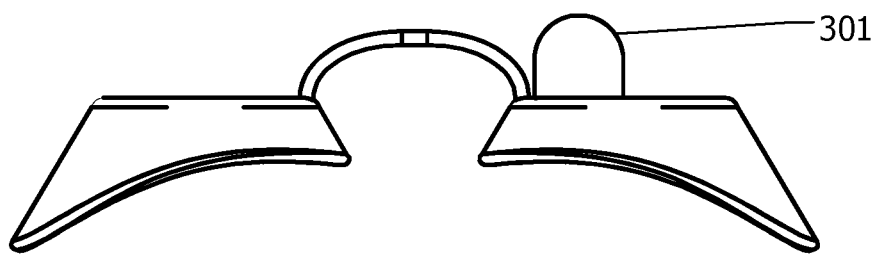
FIG. 8 is a bottom view of the display unit of FIGS. 6-7 mounted to goggles.

The image generated by the LCD 1201 is viewed by the swimmer through the 4.2 mm EFL lens 901. The field of view (FOV) in this representative embodiment is 13.3° horizontal and 4.3° vertical. It should be recognized, however, by those skilled in the art, that the FOV may be adjusted based on any number of factors such as the size and shape of the particular goggles with which module 1103 is used, as well as particular users' preference. Also, in this representative embodiment, the Largan 9498 lens 901 has an f-number of 2.8 so the exit pupil is only 1.5 mm in diameter and is located near the plane of the viewing window 1102 of the display unit. This exit pupil location allows the display unit to be placed directly on the face of the swim goggle. For example, FIG. 6 shows a pair of swim goggles 703 with display unit 301, which includes display module 1103, mounted directly to the goggle face 701.

Figure 9:
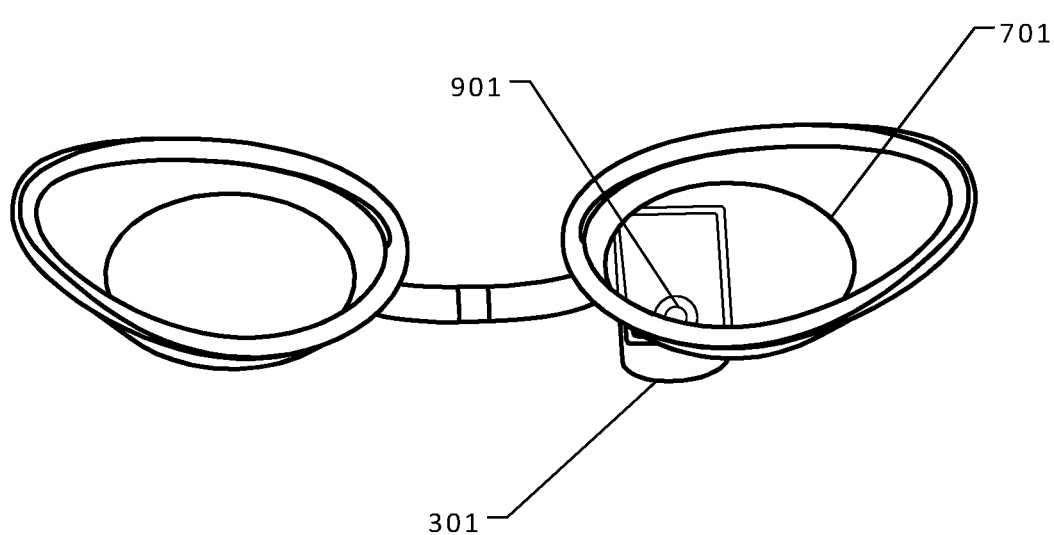
FIG. 9 is a perspective view looking through the goggles of the display unit of FIGS. 6-8 mounted to goggles.
Figure 10:
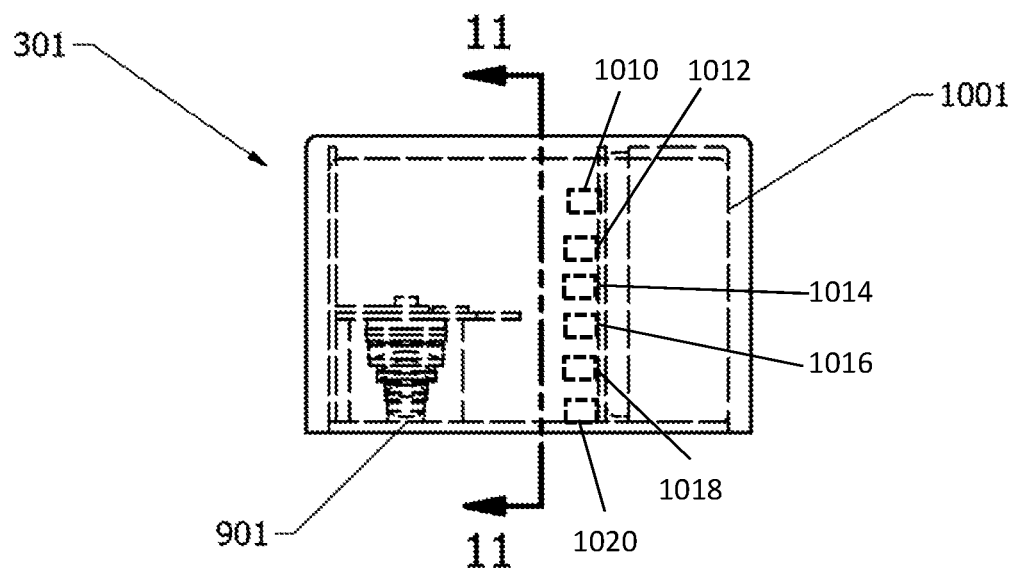
FIG. 10 is a side elevational view of the display unit of FIGS. 6-9 with internal components shown in phantom.
Figure 11:
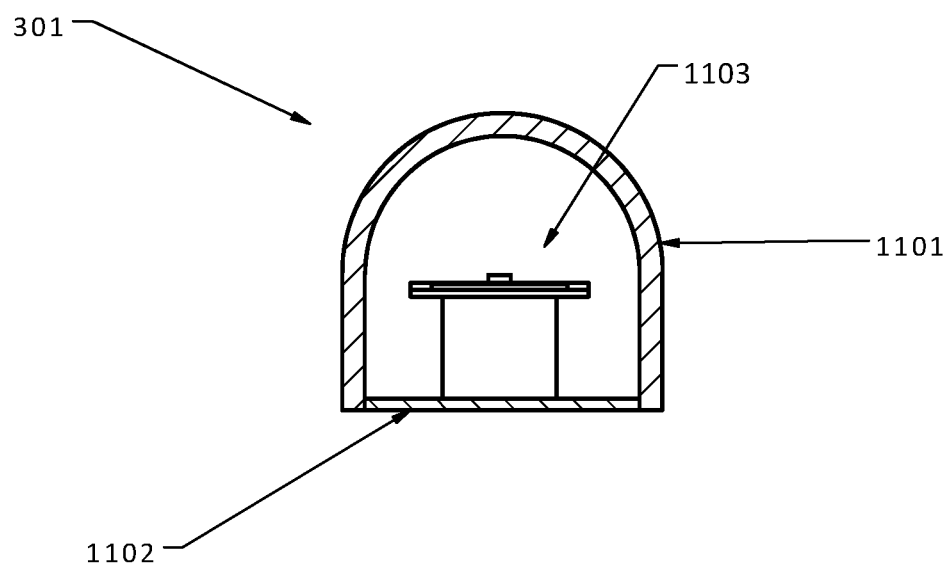
FIG. 11 is a cross-sectional view taken along 11-11 of FIG. 10.

Referring now to FIGS. 6-11, in particular embodiments, the display unit 301 is attached with a removable adhesive to the goggle face so that its viewing window 1102 is flush against the goggle face 701. Using a removable adhesive allows the display unit to be placed on new set of goggles when original set is worn out. This attachment method also allows the swimmer to position the display in front of their preferred eye and in the precise location that makes the image generated by the LCD comfortably viewable. This is particularly desirable in many applications because the compact lens 901 used in the optical display module 1103 has a small exit pupil which needs to be aligned with the swimmer's pupil to make the image generated by the LCD visible. Since even the same model of goggle will fit in a different position on different swimmers, it is desirable that the position of the display unit be customizable. FIG. 9 shows the display unit 301 viewed through the goggle.

The swimmer will typically wear the goggle while attaching the display unit to the goggle face. The swimmer can see the image generated by the LCD in the lens 901 while they are attaching the display unit to the goggle face. This allows the swimmer to easily position the display unit with no tools or measurements. Moreover, the small size of the display unit allows it to be positioned substantially anywhere on the face of the goggle. It has also been found that it may be advantageous to place the display unit in the nasal visual field as shown in FIG. 9. The display unit is less visually obtrusive to the swimmer in this location, and its proximity to the swimmer's nose and the nosepiece of the goggle helps minimize the hydrodynamic drag of the display unit. This ability to be placed in the nasal visual field contrasts with approaches that use temple mounted batteries and drive electronics that effectively force the displays to be placed in the temporal visual field where they tend to have more drag and are more obtrusive.

An aspect of the invention is the particular selection and arrangement of elements to provide for relatively low power consumption, since the inventor has recognized that low power consumption enables the use of a relatively small battery, which corresponds to the overall size of the display unit. In this representative embodiment, the EM6127 controller draws only 20 µA and the LED can produce 100 nits per µA, and is larger than the active area of the LCD. The LCD can be expected to transmit at least 25% of the incident light so an 80 µA backlight current will produce a luminance of 2000 cd/m2. The f-number of the Largan lens is less than that of the human pupil, and the exit pupil of the display will be smaller than the human pupil, so the apparent luminance of the display will be greater than 2000 cd/m2.

In total, the LED backlight and EM6127 driver consume 100 µA, two orders of magnitude less current than consumed by near-eye displays currently available for sport applications. FIG. 10 shows the display unit 301 with optical display module 1103 and a 50 mAh Varta CP 1254 rechargeable battery 1001 that can power the optical display module for 500 hours. These components fit within the 2.8 cm³ volume defined by the waterproof case 1101 of the display unit 301 and viewing window 1102 shown in FIG. 11, with space remaining for the microcontroller 1010 to drive the display 1103 (FIG. 12), the radio 1012, and sensors 1014, 1016, 1018, and the piezoelectric receiver 1020.

Since most swimming goggles do not correct for visual refractive errors, the display unit may also include a means to adjust the focus. This could be achieved by moving the LCD relative to the lens or more easily achieved by attaching a small corrective lens on the inside of the goggle opposite the optical display module lens 901. This method has the advantage of requiring no moving parts or seals in the display unit. This corrective lens could be similar to those disclosed in patent U.S. Pat. No. 6,170,952B1, but used for the novel purpose of providing focal adjustment for a sealed optical device.

It should be recognized that the speed of sound in water is relatively weakly dependent on temperature and salinity and that these conditions do not vary greatly from pool to pool. For this reason, although embodiments shown and described hereinabove include temperature and salinity sensors, such sensors may be omitted without departing from the scope of the invention. Indeed, temperature and salinity conditions don't vary rapidly with time, so the skilled artisan will recognize that the instantaneous feedback provided by these embodiments, of essentially "this stroke was better/ faster than the last" does not depend on measurement of these conditions.

Similarly, embodiments of the present invention do not necessarily need the aforementioned pressure sensors, since they are provided in the beacons 108 merely as a convenient means for determining the vertical position of the ultrasonic transducers 104 in each of the beacons 108. Embodiments of the invention may therefore omit pressure sensors from the beacons 108, and instead place their transducers at predetermined depths, or rely on tape measures or similar measurement approaches to determine the extension of conduits 103, without departing from the scope of the present invention. As also mentioned hereinabove, pressure transducers are not needed in the receiver when used in swim training (surface swimming) applications.

The present invention has been described in particular detail with respect to various possible embodiments, and those of skill in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component.

Some portions of above description present the features of the present invention in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real time network operating systems.

The present invention also relates to an apparatus for performing the operations herein. This apparatus may be specially constructed for the required purposes, or it may comprise a computer selectively activated or reconfigured by a computer program stored on a computer readable medium that can be accessed by the computer. Such a computer program may be stored in a tangible, non-transitory, computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), any other appropriate static, dynamic, or volatile memory or data storage devices, or other type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various systems may also be used with programs in accordance with the teachings herein, or it may prove convenient to construct more specialized apparatus to perform the required method steps. The required structure for a variety of these systems will be apparent to those of skill in the art, along with equivalent variations. In addition, the present invention is not described with reference to any particular programming language. It is appreciated that a variety of programming languages may be used to implement the teachings of the present invention as described herein, and any references to specific languages are provided for disclosure of enablement and best mode of the present invention.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

It should be further understood that any of the features described with respect to one of the embodiments described herein may be similarly applied to any of the other embodiments described herein without departing from the scope of the present invention.

Having thus described the invention, what is claimed is:

1. An apparatus for measuring a swimmer's speed and conveying the speed to the swimmer in real time, the apparatus comprising:
  a plurality of ultrasonic beacons each having a transducer configured to emit ultrasonic signals in a body of water within which the swimmer is swimming;
  a wearable, waterproof, ultrasonic receiver configured for being worn by the swimmer, the receiver configured to receive the ultrasonic signals emitted by the beacons and generate corresponding signal data;
  the receiver including a microcontroller communicably coupled thereto, the microcontroller configured to capture and use the signal data to calculate the swimmer's position and speed in real time;
  a wearable, waterproof, user interface device configured for being worn by the swimmer, the wearable user interface being communicably coupled to the microcontroller and configured to convey the swimmer's speed to the swimmer in real time, using one or more of visual, audible, and tactile output;
  the user interface device including a near-eye display configured for being disposed on swim goggles worn by the swimmer;
  said plurality of beacons being configured to transmit location information for the beacon originating each of said ultrasonic signals, wherein said signal data includes said location information;
  each of the plurality of beacons including an other radio, an other microcontroller, a clock, a power source, a pressure sensor, a salinity sensor, a temperature sensor, and an ultrasonic piezoelectric transducer;
  the beacons being configured to synchronize their clocks with one another by transmitting their times to one another using their other radios, wherein one of the beacons is designated a hub beacon, with remaining beacons configured to adjust their clocks to be synchronized with that of the hub beacon;

wherein upon synchronization, the beacons are configured to transmit ultrasonic signals at predetermined times at mutually distinct frequencies or modulations wherein each beacon is uniquely identifiable by the other beacons and by the receiver worn by the swimmer;

each beacon being configured to record the time of arrival of the signals received from the other beacons and to compare the time of arrival to the predetermined transmission times to calculate the signal propagation times;

each beacon being further configured to share the signal propagation times along with the depth of its transducer, temperature, and salinity, with the other beacons;

the transducer depth being determined by a pressure sensor disposed at a fixed depth relative to the transducer; and the other microcontrollers of each of the beacons are configured to use the signal propagation times between beacons along with the transducer depth to determine the relative position of each transducer by multiplying the propagation times by the of speed of sound in the body of water, with the speed of sound in the body of water being determined using the formula:

$$c = 1449.2 + 4.6t - 5.5 \times 10^{-2} t^2 + 2.9 \times 10^{-4} t^3 + (1.34 - 10^{-2} t)(S-35) + 1.6 \times 10^{-2} z$$

Where
c is the speed of sound in m/s
t is temperature in ° C.
S is salinity in ppt
z is depth in meters.

2. The apparatus of claim 1, further comprising a radio communicably coupled to the microcontroller and configured to transmit the swimmer's speed to recipients disposed remotely from the swimmer.

3. The apparatus of claim 2, wherein the radio is integrally disposed with the receiver.

4. The apparatus of claim 3, wherein the receiver comprises an accelerometer or capacitive sensor disposed in communication with the microcontroller, the accelerometer or capacitive sensor configured to automatically activate the microcontroller upon detecting movement or contact with water.

5. The apparatus of claim 4, wherein the microcontroller, radio, and user interface device are integrally disposed with the receiver within a waterproof housing.

6. The apparatus of claim 1, wherein the body of water is a swimming pool.

7. The apparatus of claim 1, wherein the signal data includes time of arrival of the ultrasonic signals.

8. The apparatus of claim 7, wherein the location information for the beacon originating each of the ultrasonic signals is embedded within the ultrasonic signals.

9. The apparatus of claim 7, wherein the microcontroller is configured to use the signal data and time of origin information for the ultrasonic signals to determine distance between the swimmer and each of the beacons in real time, using the formula:

$$D = ct$$

where
t is propagation time in seconds
D is distance in meters
c is the speed of sound in m/s.

10. The apparatus of claim 1, wherein the location information for each of the ultrasonic signals is transmitted from the ultrasonic beacons by radio to the receiver.

11. The apparatus of claim 10, wherein said plurality of ultrasonic beacons comprises at least three beacons and the microcontroller is configured to use the distance between the receiver and each of the at least three beacons to determine the location of the receiver (xa,ya,za) using the formula $$D_{a,b} = \sqrt{(x_a - x_b)^2 + (y_a - y_b)^2 + (z_a - z_b)^2}$$

where Da,b is the distance between each the receiver (a) and each beacon (b), and (xb,yb,zb) is the location of beacon (b).

12. The apparatus of claim 1, wherein the receiver comprises an ultrasonic piezoelectric receiver and a battery.

13. The apparatus of claim 1, wherein the near-eye display comprises a low-power (20 µA or less), low-pixel count (3232 pixels or less) LCD or LED array operated by the microcontroller.

14. The apparatus of claim 13, wherein the near-eye display comprises an optical display module having a liquid crystal material disposed between two layers of glass patterned with row and column electrodes, superposed with a light emitting diode and a lens.

15. The apparatus of claim 1, wherein the ultrasonic receiver and the near-eye display are integrally disposed within a housing, the housing configured for being disposed on the swim goggles.

16. The apparatus of claim 1, wherein the other microcontrollers are configured to determine distance D between each pair of beacons a,b located at coordinates (x,y,z), by using the formula:

$$D_{a,b} = \sqrt{(x_a - x_b)^2 + (y_a - y_b)^2 + (z_a - z_b)^2}.$$

17. The apparatus of claim 1, wherein once the beacons have determined their relative positions, the beacons are configured to transmit signals that allow a plurality of said receivers worn by swimmers in the body of water to determine their position and speed.

18. A method of producing an apparatus for measuring a swimmer's speed and conveying the speed to the swimmer in real time, the method comprising:
(a) configuring a plurality of ultrasonic beacons each having an ultrasonic transducer, to emit ultrasonic signals in a body of water within which the swimmer is swimming;
(b) configuring a wearable, waterproof, ultrasonic receiver for being worn by the swimmer, to receive the ultrasonic signals emitted by the beacons, and to generate corresponding signal data;
(c) communicably coupling a microcontroller to the receiver, and configuring the microcontroller to capture and use the signal data to calculate the swimmer's position and speed in real time;
(d) providing a wearable, waterproof, user interface device configured for being worn by the swimmer, and communicably coupling the wearable user interface to the microcontroller to convey the swimmer's speed to the swimmer in real time, using one or more of visual, audible, and tactile output, wherein the user interface device includes a near-eye display configured for being disposed on swim goggles worn by the swimmer;
(e) configuring the plurality of beacons to transmit location information for the beacon originating each of said ultrasonic signals, wherein said signal data includes said location information;
(f) configuring each of the plurality of beacons to include an other radio, an other microcontroller, a clock, a power source, a pressure sensor, a salinity sensor, a temperature sensor, and an ultrasonic piezoelectric transducer;

(g) configuring each of the beacons to synchronize their clocks with one another by transmitting their times to one another using their other radios, wherein one of the beacons is designated a hub beacon, with remaining beacons configured to adjust their clocks to be synchronized with that of the hub beacon;

(h) configuring the beacons wherein upon synchronization, the beacons transmit ultrasonic signals at predetermined times at mutually distinct frequencies or modulations wherein each beacon is uniquely identifiable by the other beacons and by the receiver worn by the swimmer;

(i) configuring each beacon to record the time of arrival of the signals received from the other beacons and to compare the time of arrival to the predetermined transmission times to calculate the signal propagation times;

(j) configuring each beacon to share the signal propagation times along with the depth of its transducer, temperature, and salinity, with the other beacons, the transducer depth being determined by a pressure sensor disposed at a fixed depth relative to the transducer; and (k) configuring the other microcontrollers of each of the beacons to use the signal propagation times between beacons along with the transducer depth to determine the relative position of each transducer by multiplying the propagation times by the of speed of sound in the body of water, with the speed of sound in the body of water being determined using the formula:

$$c=1449.2+4.6t-5.5\times10^{-2}t^2+2.9\times10^{-4}t^3+(1.34-10^{-2}t)(S-35)+1.6\times10^{-2}z$$

Where
c is the speed of sound in m/s
t is temperature in ° C.
S is salinity in ppt
z is depth in meters.

19. The method of claim 18, wherein the signal data includes time of arrival of the ultrasonic signals.

20. The method of claim 19, wherein the location information for the beacon originating each of the ultrasonic signals is embedded within the ultrasonic signals.

21. The method of claim 19, further comprising configuring the microcontroller to use the signal data and time of origin information for the ultrasonic signals to determine distance between the swimmer and each of the beacons in real time, using the formula:

$$D=ct$$

where
t is propagation time in seconds
D is distance in meters
c is the speed of sound in m/s.

22. The method of claim 21, further comprising calculating the speed of sound in the body of water using the formula:

$$c=1449.2+4.6t-5.5\times10^{-2}t^2+2.9\times10^{-4}t^3+(1.34-10^{-2}t)(S-35)+1.6\times10^{-2}z$$

Where
c is the speed of sound in m/s
t is temperature in ° C.
S is salinity in ppt; and
z is depth in meters.

23. The method of claim 22, wherein said plurality of ultrasonic beacons comprises at least three beacons, the method further comprising configuring the microcontroller to use the distance between the receiver and each of the at least three beacons to determine the location of the receiver (xa,ya,za) using the formula $$D_{a,b}=\sqrt{(x_a-x_b)^2+(y_a-y_b)^2+(z_a-z_b)^2}$$

where Da,b is the distance between the receiver (a) and each beacon (b), and (xb,yb,zb) is the location of each beacon (b).

24. The method of claim 18, comprising integrally disposing the ultrasonic receiver and the near-eye display within a housing configured for being disposed on the swim goggles.

25. The method of claim 18, comprising configuring the other microcontrollers to determine distance D between each pair of beacons a,b located at coordinates (x,y,z), by using the formula:

$$D_{a,b}=\sqrt{(x_a-x_b)^2+(y_a-y_b)^2+(z_a-z_b)^2}.$$

26. The method of claim 18, comprising configuring the beacons, wherein once the beacons have determined their relative positions, the beacons transmit signals that allow a plurality of said receivers worn by swimmers in the body of water to determine their position and speed.

* * * * *